United States Patent [19]

Perrior et al.

[11] Patent Number: 4,725,607

[45] Date of Patent: Feb. 16, 1988

[54] ARYL PYRIDONES AND INSECTICIDAL USE THEREOF

[75] Inventors: Trevor R. Perrior, Wokingham; Michael D. Turnbull, Reading, both of England

[73] Assignee: Imperial Chemical Industries PLC, London, England

[21] Appl. No.: 906,737

[22] Filed: Sep. 9, 1986

[30] Foreign Application Priority Data

Sep. 19, 1985 [GB] United Kingdom ............... 8523126

[51] Int. Cl.[4] .................... A61K 31/44; C07D 211/72
[52] U.S. Cl. .................... 514/345; 546/303; 546/345; 570/127
[58] Field of Search .................... 546/303; 514/345

[56] References Cited

U.S. PATENT DOCUMENTS

| | | | |
|---|---|---|---|
| 3,754,088 | 8/1973 | Witzel | 546/303 |
| 3,839,346 | 10/1974 | Gadekar | 546/303 |
| 4,546,191 | 10/1985 | Nishiyama et al. | 546/303 |

FOREIGN PATENT DOCUMENTS

| | | | |
|---|---|---|---|
| 0042696 | 12/1981 | European Pat. Off. | 546/303 |
| 038363 | 10/1983 | Japan | 546/303 |
| 72754 | 9/1984 | Japan | 546/303 |
| 186363 | 2/1985 | Japan | 546/303 |
| 1574684 | 9/1980 | United Kingdom | 546/303 |
| 2049666 | 12/1980 | United Kingdom | 546/303 |

*Primary Examiner*—Alan L. Rotman
*Assistant Examiner*—Robert C. Whittenbaugh
*Attorney, Agent, or Firm*—Cushman, Darby & Cushman

[57] ABSTRACT

Insecticidal 1-(2,6-dihalo-4-trifluoromethylphenyl)-2-pyridones and procedures for making the same.

9 Claims, No Drawings

ARYL PYRIDONES AND INSECTICIDAL USE THEREOF

This invention relates to novel aryl pyridones useful as insecticidal agents.

The invention provides novel N-aryl pyridones of formula:

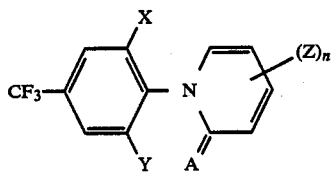
(I)

wherein each of X and Y independently represents halo, n is an integer from to 4; each Z is independently selected from halo and trihalomethyl, and A is oxygen or sulphur.

Examples of halo groups X and Y include fluoro, chloro, or bromo. Examples of groups Z include chloro, bromo, trifluoromethyl or chlorodifluoromethyl.

When n is one Z is preferably trifluoromethyl, and when n is more than one at least one Z is preferably trifluoromethyl.

Preferably n is one or two.

Preferably A is oxygen.

A preferred sub-group of compounds of formula (I) are compounds of formula (IA)

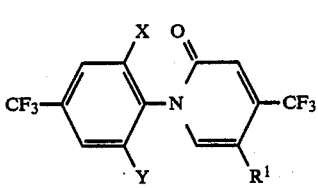
(IA)

where X and Y are as defined in relation to formula (I) and $R^1$ is halo such as chloro or bromo or trifluoromethyl.

Particular compounds according to the invention include those set out in Table I in which the meanings of X, Y and $(Z)_n$ are given for each compound.

TABLE I

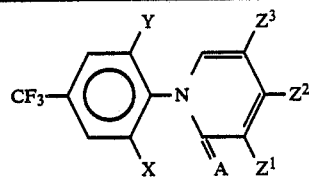

| Compound No | X | Y | A | $Z^1$ | $Z^2$ | $Z^3$ |
|---|---|---|---|---|---|---|
| 1 | F | Cl | O | Cl | H | CF₃ |
| 2 | F | Cl | O | H | H | CF₃ |
| 3 | F | Cl | O | H | H | Cl |
| 4 | F | Cl | O | Br | H | CF₃ |
| 5 | F | Cl | O | Cl | H | Cl |
| 6 | F | Cl | O | Br | H | Br |
| 7 | F | Cl | O | CF₃ | H | CF₃ |
| 8 | F | Cl | O | H | CF₃ | H |
| 9 | F | Cl | O | H | CF₃ | Cl |
| 10 | F | Cl | O | H | CF₃ | Br |
| 11 | F | Cl | O | H | CF₃ | CF₃ |
| 12 | F | Cl | O | Cl | CF₃ | Cl |
| 13 | F | Cl | O | Br | CF₃ | Br |
| 14 | F | F | O | Cl | H | CF₃ |

TABLE I-continued

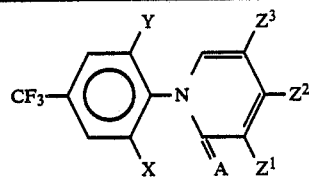

| Compound No | X | Y | A | $Z^1$ | $Z^2$ | $Z^3$ |
|---|---|---|---|---|---|---|
| 15 | F | F | O | H | H | CF₃ |
| 16 | F | F | O | H | H | Cl |
| 17 | F | F | O | Br | H | CF₃ |
| 18 | F | F | O | Cl | H | Cl |
| 19 | F | F | O | CF₃ | H | CF₃ |
| 20 | F | F | O | H | CF₃ | H |
| 21 | F | F | O | H | CF₃ | Cl |
| 22 | F | F | O | H | CF₃ | Br |
| 23 | Cl | Cl | O | Cl | H | CF₃ |
| 24 | Cl | Cl | O | CF₃ | H | CF₃ |
| 25 | Cl | Cl | O | H | CF₃ | H |
| 26 | Cl | Cl | S | H | CF₃ | H |
| 27 | Cl | Cl | O | H | CF₂Cl | H |
| 28 | Cl | Cl | O | H | CF₃ | Cl |
| 29 | Cl | Cl | O | H | CF₃ | Br |
| 30 | Cl | Cl | O | H | CF₃ | CF₃ |
| 31 | Cl | Cl | O | Cl | CF₃ | Cl |
| 32 | Cl | Br | O | H | CF₃ | H |
| 33 | Br | Br | O | H | CF₃ | H |

The compounds of formula I where A is oxygen may be prepared by reacting a compound of formula II:

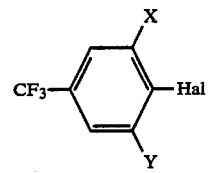
(II)

where Hal is halo and X and Y have any of the meanings given above, with a compound of formula III:

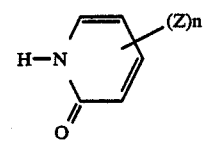
(III)

where n and Z have any of the meanings given above. The reaction is suitably carried out in the presence of a solvent and a base and optionally also a catalytic amount of a crown ether or copper depending upon the nature of the Hal group. Examples of suitable bases include alkali metal hydride, alkali metal alkoxide or an alkali metal carbonate. Examples of suitable solvents include hydrocarbon solvents, such as petroleum ether, an alcohol or an aprotic polar solvent such as dimethylformamide or dimethylacetamide.

The Hal group may be fluoro, chloro, bromo, or iodo. When Hal is iodo, copper catalysis is preferably employed to assist the reaction.

Compounds of formula (I) where n is greater than 1 can be prepared from compounds where n is 1 by halogenation using conventional conditions.

Further details of the processes for preparation of the compounds may be ascertained from the Examples set out hereinafter.

Compounds of formula (I) where A is sulphur may be obtained by reacting a compound of formula (I) where A is oxygen with a thiolating agent such as phosphorus pentasulphide. The reaction is suitably carried in an organic solvent such as pyridine at elevated temperatures of from 50° to 150° C.

Certain compounds of formula (III) are known compounds. However certain compounds of formula (III) are novel and as such form part of the invention.

Further according to the present invention there is provided a compound of formula (IIIA)

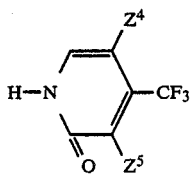

(IIIA)

wherein $Z^4$ and $Z^5$ are independently selected from hydrogen, halogen, such as chlorine or bromine, or trifluoromethyl, provided that $Z^4$ and $Z^5$ are not both hydrogen.

Examples of compounds of formula (IIIA) are set out in Table II.

TABLE II

| Compound No. | $Z^4$ | $Z^5$ |
|---|---|---|
| 37 | H | Cl |
| 38 | H | Br |
| 39 | Cl | Cl |
| 40 | Br | Br |
| 41 | H | CF$_3$ |

Compounds of formula (IIIA) where $Z^4$ and $Z^5$ are independently hydrogen or halogen are prepared by reacting 4-trifluoromethyl-2-pyridone with a halogenating agent such as halogen, N-halosuccinimide in an inert solvent such as chlorinated hydrocarbon (for example chloroform) acetonitrile, acetic acid, or sulphuric acid. The reaction is suitably carried out at temperatures of from −20° to 150° C. and may be optionally promoted by irradiation with light or by addition of a radical initiator such as azoisobutyronitrile (AIBN). Compounds of formula (IIIA) where $Z^4$ and $Z^5$ are trifluoromethyl or hydrogen, provided $Z^4$ and $Z^5$ are not both hydrogen, can be prepared by hydrolysis of a compound of formula (IV)

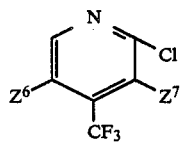

(IV)

where $Z^6$ and $Z^7$ are trifluoromethyl or hydrogen provided that $Z^6$ and $Z^7$ are not both hydrogen, for example using a base such as potassium hydroxide in a solvent such as tertbutanol or dimethylsulphoxide. Temperatures of 0° to 150° C. can be employed.

A particular example of a compound of formula IV is one in which $Z^7$ is hydrogen and $Z^6$ is trifluoromethyl (Compound 34).

Compounds of formula (IV) can be prepared by reacting a compound of formula (V)

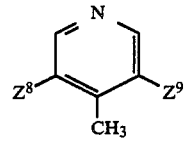

(V)

wherein $Z^8$ and $Z^9$ are hydrogen or methyl provided $Z^8$ and $Z^9$ are not both hydrogen with chlorine and anhydrous hydrogen fluoride for example using conditions described in EP-A-No. 0042696.

Further novel compounds of formula (III) are compounds of formula (IIIB)

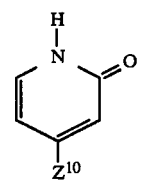

(IIIB)

where $Z^{10}$ is trihalomethyl other than trifluoromethyl, and these form part of the invention.

Compounds of formla (IIIB) can be prepared by hydrolysis of a compound of formula (VI)

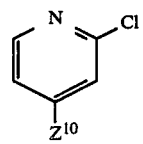

(VI)

where $Z^{10}$ is as hereinbefore defined for example using a base such as potassium hydroxide in a solvent such as tert-butanol or dimethylsulphoxide. Temperatures of 0° C. to 150° C. may be employed.

Compounds of formula (VI) are preapred by reacting 4-picoline with hydrogen fluoride and chlorine under conditions described in EP-A-No. 0042696.

Compounds of formula (II) are either known compounds or they can be prepared from known compounds by conventional methods.

Novel compounds of formula (II) and a novel precursor thereof are set out in Table III. These compounds form part of the invention.

TABLE III

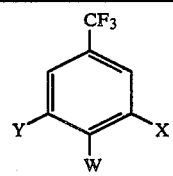

| Compound No. | X | Y | W |
|---|---|---|---|
| 42 | Br | Cl | NH$_2$ |
| 43 | Br | Cl | F |
| 44 | Br | Br | F |

They can be prepared as set out in Scheme A.

Scheme A

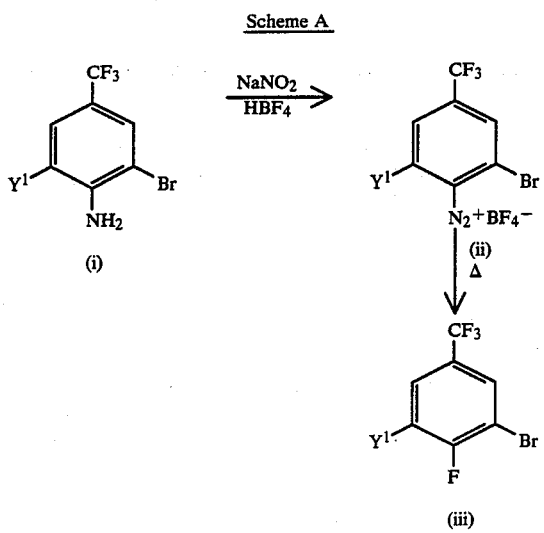

wherein $Y^1$ is chlorine or bromine. The reaction conditions are those conventionally employed and are illustrated in the preparations hereinafter.

Compounds of formula (i) where $Y^1$ is chlorine can be prepared by bromination of a compound of formula

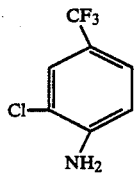

The compounds of formula I may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the nonionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5-2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin in particular, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, pralethrin and 5-benzyl-3-furylmethyl-(E)-(1R,3S)-2,2-dimethyl-3-(2-oxothiolan-3-ylidenemethyl) cyclopropane carboxylate; Organophosphates such as profenofos, sulprofos, methyl parathion, azinphos.

(b) methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphos-methyl, fenitrothion or diazionon;

(c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;

(d) Benzoyl ureas such as triflumeron, or chlorofluazuron;

(e) Organic tin compounds such as cyhexatin, fenbutatin oxide, azocyclotin;

(f) Macrolides such as avermectins or milbemyins, for example such as avamectin, avermectin, and milbemycin;

(g) Hormones such as pheromones;

(h) Organochlorine compounds such as benzene hexachloride, DDT, chlordane or dieldrin; or (i) Amidines such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, motilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamax, and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compositions of the invention are toxic to a variety of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
*Aonidiella* spp. (scale insects)
*Trialeuroides* spp. (white flies)
*Blattella germanica* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
*Chilo partellus* (maize stem borers)

The compounds of formula I and compositions comprising them have shown themselves to be particularly useful in controlling public health pests such as flies and cockroaches. Certain compounds of formula (I) and compositions comprising them are useful against pests in rice crops, such as rice hoppers. They may also be active against organophosphate and pyrethroid resistant strains of pests such as houseflies (*Musca domestica*). Thus compounds 2 to 6, 8, 14, 17, 18, 20, 23, 25 of table I gave 100% mortality when sprayed onto adult houseflies (*Musca domestica*) in this form of an aqueous composition comprising 500 ppm of the compound. The said compounds were also effective as knock-down agents when applied to mosquitoes (*Aedes aegyptii*) in the March and Kearns test at 500 ppm. In addition compounds 1, 4, 8, 14, 17, 23 and 25 were effective againts cockroach nymphs (*Blattella germanica*) giving 100% mortality at a rate of 500 ppm. They may also be useful in combating insect and acarine pests which infest domestic animals, such as *Lucilia sericata*, and ixodid ticks such as *Boophilus* spp., *Ixodes* spp., *Amblyomma* spp., *hipicephalus* spp., and *Dermaceutor* spp. They may be effective in combating both susceptible and resistant strains of these pests in their adult, larval and intermediate stages of growth, and may be applied to the infested host animal by topical, oral or parenteral administration. The compounds of formula (I) and compositions containing them also show nematocidal activity.

The following Preparations and Examples illustrate various aspects of this invention. In the Preparations and Examples the products were usually identified and characterised by means of nuclear magnetic resonance spectroscopy and infra red spectroscopy. In each case where a product is specifically named its spectral characteristics are consistent with the assigned structure.

Preparation 1

2-Chloro-4,5-bis(trifluoromethyl)pyridine (Compound No. 34) was prepared according to the general method disclosed in EP-A-No.42696.

A vertical fluidised-bed reactor made of Inconel was charged with aluminium trifluoride (8-250) which was activated by pre-treatment with hydrogen fluoride gas at a rate of four moles per hour and at a temperature of 390° C. for one hour.

The reactor was heated at 400° C. and 3,4-lutidine, nitrogen, chlorine and hydrogen fluoride gas were fed into the reactor at a rate of 0.3 moles per hour of the lutidine and molar ratio of nitrogen, chlorine and hydrogen fluoride to the lutidine of 6:10:131 for twelve hours. The liquid condensate from the reactor was neutralised with 20% Potassium hydroxide solution and carefully distilled, collecting the fraction with a boiling range of 73°-74° C. at 46 mm Hg. This fraction was purified by chromatography on silica with a mixture 10% diethyl ether and petrol (30°-40° C. boiling range) as eluent. The component with Rf=0.5 was collected and distilled at atmospheric pressure to give the required compound bp. 148° C.; $\delta$ (CDC$_3$) 8.84 (1H,s); 7.73 (1H,s).

Preparation 2

2-Chloro-4-chlorodifluoromethylpyridine (Compound No. 35) was made according to the general method of Preparation 1 except that the reactor was heated at 350° C.; 4-picoline was introduced into the reactor at a rate of 0.8 mol per hour; the molar ratios of nitrogen, chloride and hydrogen chloride to picoline were 1:3:61 and the reaction was continued for 25 hours. The neutralised liquid condensate was fractionally distilled to give 2-chloro-4-trifluoromethylpyridine (bp. 145°-146° C.), 2,6-dichloro-4-trifluoromethylpyridine (bp. 168°-170° C.) and the desired compound (bp. 173° C.).

Preparation 3

This Example illustrates the preparation of 4-(chlorodifluoromethyl)-2-pyridone (Compound No. 35).

2-Chloro-4-(chlorodifluoromethyl)pyridine (10 g, 51 mmol), finely ground potassium hydroxide (5.7 g, 100 mmol) and tert. butanol (100 ml) were mixed rapidly at room temperature. The mixture was refluxed for 6 hours.

The tert. butanol was evaporated in vacuo and the residue treated with water (100 ml) and extracted with ethylacetate (2×100 ml). The combined organic extracts were washed with water (3×100 ml), dried over magnesium sulphate and evaporated in vacuo to give a white solid. Recrystallisation from ethylacetate gave a pure sample of the required compound (5.5 g, mp=140.1°-141.1° C.); $\delta$ (d$_6$-acetone/DMSO) 11 (1H,brs); 6.68 (1H,m); 6.64 (1H,d); 6.4 (h,dd).

Preparation 4

This illustrates the preparation of 5-chloro-4-trifluoromethyl-2-pyridone. (Compound No. 37, Table II).

A mixture of 4-trifluoromethyl-2-pyridone (10.2 g, 62.5 mmol), N-chlorosuccinimide (8.4 g, 62.9 mmol) and chloroform (45 ml) was heated at reflux for 2 hours. The reaction mixture was filtered and the filtrate evaporated in vacuo to give a white solid which was extracted with ethyl acetate. The ethyl acetate solution was washed with water and brine, dried over agnesium sulphate and evaporated in vacuo. The residue was recrystallised from a mixture of acetone and petrol to give the required compound (8.5 g, mp. 173.5°-174.5° C.); $\delta$ (d$_6$-DMSO) 7.94 (1H,s); 6.95 (1H,s).

Preparation 5

This illustrates the preparation of 5-bromo-4-trifluoromethyl-2-pyridone (Compound No. 38, Table II).

Bromine (6.3 ml, 0.122 mol) was added to a solution of 4-trifluoromethyl-2-pyridone (10 g, 61 mmol) in acetic acid (20 ml). The reaction mixture was heated under reflux for two hours, allowed to cool, and poured into aqueous sodium thiosulphate solution. The aqueous mixture was extracted with ethyl acetate, washed with brine, saturated aqueous sodium bicarbonate and again with brine, dried over magnesium sulphate and evaporated in vacuo. The residue was recrystallised from a mixture of ethyl acetate and petrol to give the required compound (6.3 g);.$\delta$ (CDCl$_3$/d$_6$-DMSO) 7.72 (1H,s); 6.90 (1H,s).

Preparation 6

This illustrates the preparation of 3,5-dichloro-4-trifluoromethyl-2-pyridone (Compound No. 39, Table II).

A solution of 4-trifluoromethyl-2-pyridone (10 g, 61 mmol) and N-chlorosuccinimide (NCS) (8.6 g, 64.4 mmol) in acetonitrile (45 ml) was heated under reflux for one hour. An additional portion of NCS (8 g, 60 mmol) was added and the heating continued for four hours when a further portion of NCS (3.5 g, 26 mmol) was added and the reaction heated for a final hour. The acetonitrile was evaporated in vacuo, the residue dissolved in water and extracted with ethyl acetate. The organic layers were washed with water, then brine, dried over magnesium sulphate and evaporated in vacuo to give an orange gum which crystallised on standing. Yellow crystals of impure (33) were obtained by trituration with petrol. The triturate was evaporated in vacuo and the residual gum purified by chromatography on silica eluting with 5% methanol-dichloromethane to give a further crop of (33). The two batches were combined and recrystallised from acetone/petrol mixture to give the required compound (3 g, mp. 181.9°-182.8° C.); $\delta$ (d$_6$-acetone) 7.9 (1H,s).

Preparation 7

This illustrates the Preparation of 3,5-dibromo-4-trifluoromethyl-2-pyridone, (Compound No. 40, Table II).

A mixture of 4-trifluoromethyl-2-pyridone (5 g, 31 mmol) and N-bromosuccinimide (13.7 g, 77 mmol) in chloroform (50 ml) was heated at reflux under a nitrogen atmosphere for one hour. When cool the reaction mixture was poured into water and extracted with chloroform. The organic layers were washed with water, dried over magnesium sulphate and evaporated in vacuo to give the crude product which was purified by trituration with a mixture of ethyl acetate and petroleum ether. Further product was obtained on purification of the triturate by chromatography (ethylacetate/silica) and trituration. The combined crops of product (4.31 g) showed $\delta$ (d6-acetone) 8.0 (s).

Preparation 8

This illustrates the preparation of 4,5-bis(trifluoromethyl)-2-pyridone (Compound No. 41, Table II).

The general method of preparation 3 was used to hydrolyse 2-chloro-4,5-bis(trifluoromethyl)pyridine, except that the reaction mixture was stirred at room temperature for 24 hours and then heated at 80° C. for three hours. The crude product was purified by chromatography on silica with a 10% methanol-dichloromethane mixture as eluent to give the required compound as a white solid (340 mg, mp. 173.7°–175.0° C.); δ (CDCl$_3$/d$_6$-DMSO) 7.8 (1H,s); 6.95 (1H,s).

Preparation 9

This Example illustrates the preparation of 2-bromo-6-chloro-4-trifluoromethyl aniline (Compound No. 42, Table III).

2-Chloro-4-trifluoromethyl aniline (5 g, 26 mmol) and glacial acetic acid (60 ml) were mixed at room temperature and then cooled to 15° C. Bromine (4.1 g, 26 mmol) was added dropwise to the rapidly stirred mixture. The reaction was warmed to room temperature and stirred for another hour. A thick white precipitate was formed.

Sodium metabisulphite (2 g) was added. The reaction was filtered and the white solid treated with saturated sodium bicarbonate solution (200 ml), and extracted with ether (2×100 ml). The combined organic extracts were washed with saturated sodium bicarbonate solution (50 ml), and water (2×50 ml), dried over magnesium sulphate and evaporated in vacuo to give a colourless oil (3.5 g) δ (CDCl$_3$) 7.54 (2H,dm); 4.83 (2H,brs).

Preparation 10

This Example illustrates the preparation of 3-bromo-5-chloro-4-fluorobenzotrifluoride (Compound No 43, Table III).

2-Bromo-6-chloro-4-trifluoromethylaniline (19.7 g, 72 mmol) was added to a rapidly stirred 40% fluoroboric acid solution (40 ml) at −5° to −0° C. Sodium nitrite (4.95 g, 72 mmol) dissolved in water (8 ml) was added dropwise to the mixture, maintaining the temperature below 0° C. The reaction was stirred at 0° C. for 4 hours.

The reaction was filtered under suction and the yellow solid washed with cold methanol (2×20 ml) and cold diethyl ether (2×20 ml). The white solid was dried over P$_2$O$_5$ under vacuum overnight to give a pure sample of 2-bromo-6-chloro-4-trifluoromethyl benzene diazonium tetrafluoroborate. (20 g) ‖ max (nujol) 2300 cm$^{-1}$.

2-Bromo-6-chloro-4-trifluoromethylbenzenediazonium tetrafluoroborate (20 g, 59 mmol) was pyrolysed using a microburner in two batches (2×10 g).

The residue from the pyrolysis was treated with water (20 ml) and saturated sodium bicarbonate solution (20 ml) and extracted with diethyl ether (2×50 ml). The combined organic extracts were washed with saturated sodium bicarbonate solution (25 ml) and water (2×25 ml), dried over magnesium sulphate and the diethyl ether removed by flash distillation.

Distillation in a Kugelrohr apparatus gave a pure sample of the required product (3.7 g, bp 130°–140° C.). δ(CDCl$_3$), 7.76 (1H,dd); 7.66 (1H,dd).

Preparation 11

This illustrates the preparation of 3,5-dibromo-4-fluorobenzotrifluoride (Compound No. 44, Table III) from 2,6-dibromo-4-trifluoromethyl aniline. The method of Preparation 10 was used except that 2,6-dibromo-4-trifluoromethylbenzenediazonium tetrafluoroborate was prepared in a 1:1 mixture of 40% fluoroboric acid and water. The required compound showed δ(CDCl$_3$) 7.8 (2H,dq).

EXAMPLE 1

This Example illustrates the preparation of 1-(2,6-difluoro-4-trifluoromethylphenyl)-4-trifluoromethyl-2-pyridone (Compound No. 20, Table I).

A well stirred mixture of 4-trifluoromethyl-2-pyridone (1.5 g, 9.2 mmol), 3,4,5-trifluorobenzo trifluoride (9.2 g, 46 mmol) and potassium carbonate (6.3 g, 46 mmol) in dimethylformamide (40 ml) was heated at 100° C. under nitrogen for 5 hours. The reaction mixture was poured into water (100 ml), acidified with dilute hydrochloric acid and extracted with chloroform (2×75 ml). The combined organic layers were washed with water (3×100 ml) dried over magnesium sulphate and evaporated in vacuo. The resulting oil was purified by column chromatography on silica with 2:1 petrol - diethyl ether eluent followed by crystalisation from a petrol - diethyl ether mixture to give the required compound as a white solid (680 mg, mp 136°–137° C.);δ(d$_6$-acetone), 8.10 (1H,m); 7.9 (2H,d); 7.1 (1H,m); 6.76 (1H,dd).

EXAMPLE 2

The following compounds were prepared by the method of Example 1 from the appropriate compounds of formula II (Hal represents fluoro) and formula III:

(i) 1-(2-Chloro-6-fluoro-4-trifluoromethylphenyl)-3-chloro-5-trifluoromethyl-2-pyridone (Compound No. 1, Table I), expect that the reaction was heated at 80° C. for six hours. The compound showed mp. 117°–117.5° C.; δ(d$_6$-acetone) 8.42 (1H,m); 8.21 (1H,d); 8.05 (1H,s); 8.0 (1H,d).

(ii) 1-(2-Chloro-6-fluoro-4-trifluoromethylphenyl)-3,5-dibromo-2-pyridone (Compound No. 6, Table I), except that the reaction was heated at 110° C. for four hours. The compound showed mp. 148.8°–149.2° C.; δ(d$_6$-acetone) 8.12 (1H,d); 8.05 (1H,d); 8.0 (1H,s); 7.9 (1H,d).

(iii) 1-(2,6-Difluoro-4-trifluoromethylphenyl)-3-chloro-5-trifluoromethyl-2-pyridone (Compound No. 14, Table I), except that the reaction was heated at 140° C. for six hours. The compound showed mp. 104°–105° C.; δ(d$_6$-acetone) 8.4 (1H,m); 8.1 (1H,d); 7.75 (2H,d).

(iv) 1-(2,6-Difluoro-4-trifluoromethylphenyl)-5-chloro-2-pyridone (Compound No. 16, Table I) except that the reaction was heated at 100° C. for two hours. The compound showed mp. 152°–153° C.; δ(CDCl$_3$) 7.40 (2H,d); 7.40 (1H,dd); 7.22 (1H,dd); 7.63 (1H,dd).

(v) 1-(2,6-difluoro-4-trifluoromethylphenyl)-3,5-bis-(trifluoromethyl)-2-pyridone (Compound No. 19, Table I) except that the reaction was heated at 80° C. for sixteen hours and then at 100° C. for twenty-four hours. The compound W showed δ(CDCl$_3$) 8.00 (1H,s); 7.80 (1H,s); 7.44 (2H,d).

(vi) 1-(2,6-difluoro-4-trifluoromethylphenyl)-5-chloro-4-trifluoromethyl-2-pyridone (Compound No. 21, Table I), except that the reaction was heated at 80° C. for twelve hours. The compound showed: δmp. 134.9°–136° C. δ(d$_6$-acetone) 8.20 (1H,s); 7.80 (2H,d); 7.12 (1H,s).

(vii) 1-(2,6-Difluoro-4-trifluoromethylphenyl)-5-bromo-4-trifluoromethyl-2-pyridone (Compound No. 22, Table I) except that the reaction was heated at 80° C. for six hours and then at 100° C. for ten hours. The compound showed δ(CDCl$_3$) 7.47 (2H,d); 7.40 (1H,s); 7.1 (1H,s).

EXAMPLE 3

This Example illustrates the preparation of 1-(2-chloro-6-fluoro-4-trifluoromethylphenyl)-4-trifluoromethyl-2-pyridone (Compound No. 8, Table I).

Sodium Hydride (0.33 g of a 50% dispersion in mineral oil, 6.7 mmol) was washed with light petrol (2×5 ml) in a dry flask flushed with nitrogen. Dimethylformamide (20 ml) was added and the mixture gently stirred at room temperature whilst 4-trifluoromethyl-2-pyridone (1 g, 6.1 mmol) was added slowly portionwise. After a further hour at room temperature 3-chloro-4,5-difluorobenzotrifluoride (4.3 g, 20 mmol) was added and the mixture warmed to 50° C. for 3 hours. The reaction mixture was carefully diluted with water (100 ml), acidified with dilute hydrochloric acid and extracted with chloroform (2×75 ml). The combined organic extracts were washed with water (3×100 ml), dried over magnesium sulphate and evaporated in vacuo to give a white oily solid. Chromatography on silica with 4:1 petrol - diethyl ether eluent followed by recrystalisation from cyclohexane gave a pure sample of the required compound (200 mg, mp 145.5°–146.5° C.);$\delta$(d$_6$-acetone) 7.92 (1H,brs); 7.78 (1H,d); 7.63 (1H,d); 7.00 (1H,m); 6.62 (1H,dd).

EXAMPLE 4

By the use of procedures similar to that illustrated in Example 3 the following compounds were prepared from the appropriate compounds of formula II (Hal representing fluoro) and formula IV:

(i) 1-(2-Chloro-6-fluoro-4-trifluoromethylphenyl)-5-trifluoromethyl-2-pyridone (Compound No. 2 Table I) except that the reaction was heated at 50° C. for three hours and then 80° C. for five hours. The compound showed mp. 132.6°–133° C.; $\delta$(d$_6$- acetone); 8.32 (1H,brs); 7.95 (2H,brs); 7.9 (1H,dd); 6.8 (1H,d).

(ii) 1-(2-Chloro-6-fluoro-4-trifluoromethylphenyl)-5-chloro-2-pyridone (Compound No. 3, Table I) except that the reaction was heated at 50° C. for five hours and then at 90° C. for 16 hours. The compound showed mp. 143°–143.9° C.; $\delta$(CDCl$_3$) 7.65 1H,m); 7.45 (1H,m); 7.42 (1H,dd); 7.18 (1H,d); 6.62 (1H,d).

(iii) 1-(2-Chloro-6-fluoro-4-trifluoromethylphenyl)-3-bromo-5-trifluoromethyl-2-pyridone (Compound No. 4, Table I) except that the reaction was heated at 80° C. for eight hours and then at 100° C. for sixteen hours. The compound showed mp. 99.9°–100.3° C.; $\delta$(d$_6$- acetone 8.5 (1H,m); 8.45 (1H,m); 8.1 (1

(iv) 1-(2-Chloro-6-fluoro-4-trifluoromethylphenyl)-3,5-dichloro-2-pyridone (Compound No. 5, Table I) except that the reaction was heated at 110° C. for six hours. The compound showed mp. 143.2°–144.1° C.; $\delta$(CDCl$_3$) 7.68 (1H,s); 7.62 (1H,d); 7.5 (1H, dd); 7.15 (1H,d).

(v) 1-(2-Chloro-6-fluoro-4-trifluoromethylphenyl)-3,5-bis(trifluoromethyl)-2-pyridone (Compound No. 7, Table I) except that the reaction was heated at 80° C. for sixteen hours. The compound showed mp. 114.0°–114.8° C.; $\delta$(d$_6$-acetone) 8.72 (1H,s); 8.40 (1H,s); 8.04 (1H,s); 7.96 (1H,d).

(vi) 1-(2-Chloro-6-fluoro-4-trifluoromethylphenyl)-5-bromo-4-trifluoromethyl-2-pyridone (Compound No. 10, Table I) except that the reaction was heated at 100° C. for sixteen hours. The compound showed mp. 119°–120° C.; $\delta$(CDCl$_3$) 7.7 (1H,s); 7.5 (1H,d); 7.45 (1H,s); 7.1 (1H,s).

(vii) 1-(2-Chloro-6-fluoro-4-trifluoromethylphenyl)-4,5-bis(trifluoromethyl)-2-pyridone (Compound No. 11, Table I) except that the reaction was heated at 90° C. for twenty-four hours. The compound showed $\delta$(d$_6$-acetone) 8.6 (1H,s); 8.0 (1H,m); 7.9 (1H,m ; 7.25 (1H,s).

(viii) 1-(2-Chloro-6-fluoro-4-trifluoromethylphenyl)-3,5-dichloro-4-trifluoromethyl-2-pyridone (Compound No. 12, Table I) except that the reaction was heated at 90° C. for 48 hours. The compound showed mp. 179.7°–180.9° C., $\delta$(d$_6$-acetone/CDCl$_3$) 8.0 (1H,s); 7.85 (1H,m); 7.8 (1H,dd).

(ix) 1-(2-Chloro-6-fluoro-4-trifluoromethylphenyl)-3,5-dibromo-4-trifluoromethyl-2-pyridone (Compound No. 13, Table I) except that the reaction was heated at 80° C. for sixteen hours. The compound showed mp. 176.3°–176.8° C.; $\delta$(d$_6$-acetone) 8.44 (1H,s); 8.40 (1,d); 8.12 (1H,s).

(x) 1-(2,6-Dichloro-4-trifluoromethylphenyl)-3-chloro-5-trifluoromethyl-2-pyridone (Compound No. 19, Table I) except that the reaction heated at 100° C. for twelve hours. The compound showed mp. 134.2°–134.8° C.; $\delta$(d$_6$-acetone) 8.50 (1H,m); 8.30 (1H,d); 8.22 (2H,s).

(xi) 1-(2,6-Dichloro-4-trifluoromethylphenyl)-3,5-bis(trifluoromethyl)-2-pyridone (Compound No. 24, Table I) except that the reaction was heated at 95° C. for sixteen hours. The compound showed mp. 146.2°–147.0° C.; $\delta$(d$_6$-acetone) 8.50 (1H,m); 8.42 (1H,m); 8.16 (2H,s).

(xii) 1-(2,6-Dichloro-4-trifluoromethylphenyl)-4-trifluoromethyl-2-pyridone (Compound No. 25) except that the reaction was stirred at 20° C. for 2 hours and then heated at 80° C. for three hours. The compound showed mp. 143.6°–144.1° C.; $\delta$(d$_6$-acetone) 8.1 (2H,brs); 7.92 (1H,d); 7.1 (1H,m); 6.8 (1H,dd).

(xiii) 1-(2,6-Dichloro-4-chlorodifluoromethyl-2-pyridone (Compound No. 27, Table I) except that the reaction was heated at 80° C. for twenty hours. The compound showed mp. 146.7°–147.2' C.; $\delta$(d$_6$-acetone) 8.10 (2H,s); 7.8 (1H,dm); 6.92 (1H,m); 6.64 (1H,dd).

(xiv) 1-(2,6-Dichloro-4-trifluoromethylphenyl)-5-chloro-4-trifluoromethyl-2-pyridone (Compound No. 28, Table I) except that the reaction was heated at 90° C. for 21 hours. The compound showed mp. 149°–151° C.; $\delta$(CDCl$_3$); 8.12 (3H,s); 7.18 (1H,s).

(xv) 1-(2,6-Dichloro-4-trifluoromethylphenyl)-5-bromo-4-trifluoromethyl-2-pyridone (Compound No. 29, Table I) except that the reaction was heated at 90° C. for 21 hours. The compound showed mp. 147°–149° C.; $\delta$(d$_6$- acetone) 8.21 (1H,s); 8.12 (2H,s); 7.18 (1H,s).

(xvi) 1-(2,6-Dichloro-4-trifluoromethylphenyl)-4,5-bis-(trifluoromethyl)-2-pyridone (Compound No. 30, Table I) except that the reaction was heated at 90° C. for sixteen hours. The compound showed mp. 129.2°–131.3° C.; $\delta$(d$_6$-acetone) 8.6 (1H,s); 8.1 (2H,s); 7.25 (1H,s).

(xvii) 1-(2,6-Dichloro-4-trifluoromethylphenyl)3,5-dichloro-4-trifluoromethyl-2-pyridone (Compound No. 31, Table I) except that the reaction was heated at 90° C. for 48 hours. The compound showed mp. 202.1°–203.2° C.; $\delta$(d$_6$-acetone) 8.15 (1H,s); 8.10 (2H,s).

(xviii) 1-(2-Bromo-6-chloro-4-trifluoromethylphenyl)-4-trifluoromethyl-2-pyridone (Compound No. 32, Table I) except that the reaction was heated at 90° C. for sixteen hours. The compound showed mp. 151.2°–151.8° C.; $\delta$(d$_6$-acetone) 8.32 (1H,s); 8.04 (1H,s); 7.92 (1H,dm); 7.12 (1H,m); 6.8 (1H,dd).

(xix) 1-(2,6-Dibromo-4-trifluoromethylphenyl)-4-trifluoromethyl-2-pyridone (Compound No. 33, Table I) except that the reaction was heated at 80° C. for 21 hours. The compound showed mp. 155.8°–156.5° C.; (d$_6$-acetone) 8.24 (2H,s); 7.80 (1H,dm); 6.98 (1H,m); 6.7 (1H,dd).

EXAMPLE 5

This Example illustrates the preparation of Compound No. 20, Table I by an alternative procedure to that illustrated in Example I. To a solution of sodium metal (40 mg, 6.1 mmol) in ethanol (10 ml) was added 4-trifluoromethyl-2-pyridone (1 g, 6.1 mmol) portionwise. After stirring at room temperature for 1 hour the ethanol was removed in vacuo and the residue dissolved in dry dimethylacetamide (10 ml). 3,4,5-Trifluorobenzotrifluoride (2.4 g, 12 mmol) was added and the solution heated at 110° C. for 4 hours. The dimethylacetamide was removed in vacuo and the residue treated with water (20 ml) and chloroform (50 ml). The chloroform layer was washed with water (3×30 ml) dried and evaporated. The residue was chromatographed on silica with 4:1 petrol-diethyl ether and then recrystalised from petrol-diethyl ether to give the required compound (220 mg).

EXAMPLE 6

By the use of a similar procedure to that shown in Example 5 the following compounds were prepared from the appropriate compounds of formula II (Hal represents fluorine) and formula III:

(i) 1-(2,6-Difluoro-4-trifluoromethylphenyl)-5-trifluoromethyl-2-pyridone (Compound No. 15, Table I) except that the reaction was heated at 130° C. for three hours. The compound showed mp. 118.6°–119.2° C.; δ(d6-acetone) 8.5 (1H,m); 7.9 (1H,dd); 7.85 (2H,d); 6.9 (1H,d).

(ii) 1-(2,6-Difluoro-4-trifluoromethylphenyl)-3,5-dichloro-2-pyridone (Compound No. 18, Table I) except that the reaction was heated at 110° C. for ten hours. The compound showed mp. 132.8°–134.2° C.; δ(CDCl$_3$) 7.7 (1H,d); 7.44 (2H,d); 7.2 (1H, brd).

EXAMPLE 7

This Example illustrates the preparation of 1-(2,6-difluoro-4-trifluoromethylphenyl)-3-bromo-5-trifluoromethyl-2-pyridone (Compound No. 17, Table I).

Bromine (800 mg, 5 mmol) was added to a solution of 1-(2,6-difluoro-4-trifluoromethylphenyl-5-trifluoromethyl-2-pyridone (1.7 g, 5 mmol) in dry dimethyl formamide (20 ml). The reaction mixture was heated at 120° C. for 3 hours, allowed to cool, and the solvent resolved in vacuo to give a residual oil which was taken up in chloroform (30 ml) and washed with water (30 ml). The organic layer was dried, evaporated and the residue crystalised from petrol to give the required compound (260 mg, mp 87.5°–88° C.).

EXAMPLE 8

This Example illustrates the preparation of 1-(2-chloro-6-fluoro-4-trifluoromethylphenyl)-5-chloro-4-trifluoromethyl-2-pyridone (Compound No. 9, Table I).

Sodium hydride (0.54 g of a 50% dispersion in mineral oil, 11 mmol) was washed with diethyl ether in a dry flask flushed with nitrogen. Dimethylformamide (5 ml) was added and the mixture gently stirred at room temperature whilst a solution of 5-chloro-4-trifluoromethyl-2-pyridone (2 g, 10 mmol) in dimethylformamide (15 ml) was added dropwise. 1,4,7,10,13-Pentaoxacyclopentadecane (0.4 ml, 2 mmol) was added, followed by 3-chloro-4,5-difluorobenzotrifluoride (4.4 g, 20 mmol) and the mixture heated at 85° C. for 24 hours. The reaction mixture was carefully poured into water and extracted with ethyl acetate. The organic extract was washed with brine, dried over magnesium sulphate and evaporated in vacuo to give an oily residue which was triturated with petrol. The solid thereby produced was purified by recrystallisation from ethyl acetate-petrol to give the required compound (960 mg). The compound showed mp. 128.5°–129.7° C.; (CDCl$_3$) 7.7 (1H,s); 7.5 (1H,dd); 7.3 (1H,d); 7.1 (1H,s).

EXAMPLE 9

This Example illustrates the preparation of 1-(2,6-dichloro-4-trifluoromethylphenyl)-4-trifluoromethyl-2-thiopyridone (Compound No. 26, Table I).

1-(2,6-Dichloro-4-trifluoromethylphenyl)-4-trifluoromethyl-2-pyridone (Compound No. 25, Table I) (0.3 g, 0.8 mmol) was dissolved in pyridine (1.2 ml). Nitrogen gas was bubbled through the solution until it was well purged. Phosphorous pentasulphide (0.25 g, 1.13 mmol) was added and the solution heated under reflux for 24 hours. The reaction mixture was allowed to cool, water was added and the reaction gently warmed for a few minutes. Extraction with ethyl acetate, followed by drying of the organic layers with magnesium sulphate and evaporation in vacuo gave a crude residue which was carefully purified by chromatography on silica gel with 5% diethyl ether in petrol as eluent, followed by trituration with petrol to give the required compound (6 mg), δ(d$_6$ - acetone) 8.0 (1H,d); 7.95 (2H,s); 7.7 (1H,d); 7.05 (1H,dd).

Biological Data

The insecticidal activity of compounds of formula (I) is set out in the following Table IV as a grading of A, B or C where A indicates that 80–100% mortality was observed, B indicates that 50–79% mortality was observed and C indicates that 0–49% mortality was observed. The tests were conducted by spraying a suitable support medium (eg. leaves of a suitable food plant, or filter paper) with a solution of the compound under test and placing the pests thereon. Assessment of mortality was made 72 hours after spraying. In the test the compounds were used in the form of aqueous composition prepared by dissolving the compound in mixture of solvents consisting of 1 part by volume by acetone and 1 part by volume of ethanol and diluting the solution with water containing 0.1% by volume of a wetting agent ("Synperonic" NX - "'Synperonic" is a Registered Trade Mark).

TABLE IV

| Compound No. | Rate of Application | Insecticidal Activity Species (see Table V) | | | | | |
| --- | --- | --- | --- | --- | --- | --- | --- |
| | | NL | MD | BG | HV | CPA | DB |
| 1 | 500 | C | A | A | C | C | C |
| 2 | 500 | C | A | B | C | C | C |
| 3 | 500 | C | A | C | C | C | C |
| 4 | 500 | C | A | A | C | C | C |
| 5 | 500 | B | A | C | C | C | C |
| 6 | 500 | C | A | C | A | B | C |
| 7 | 500 | C | C | C | C | — | C |
| 8 | 500 | A | A | A | C | A | C |
| 9 | 500 | A | A | A | A | A | B |

TABLE IV-continued

| Compound No. | Rate of Application | Insecticidal Activity Species (see Table V) | | | | | |
|---|---|---|---|---|---|---|---|
| | | NL | MD | BG | HV | CPA | DB |
| 10 | 500 | A | A | A | B | A | C |
| 11 | 250 | C | A | A | B | — | C |
| 12 | 500 | A | C | A | C | C | C |
| 13 | 500 | C | C | C | C | — | C |
| 14 | 500 | B | A | A | C | C | A |
| 15 | 500 | C | C | C | C | C | C |
| 16 | 500 | C | B | C | C | C | C |
| 17 | 500 | C | A | A | C | C | C |
| 18 | 500 | C | A | B | B | C | C |
| 19 | 440 | C | C | C | C | — | A |
| 20 | 500 | C | A | A | C | A | C |
| 21 | 500 | C | A | A | A | A | C |
| 22 | 500 | A | A | A | B | A | B |
| 23 | 500 | B | A | A | C | A | C |
| 24 | 500 | C | C | C | C | — | C |
| 25 | 500 | A | A | A | A | A | — |
| 26 | 500 | C | A | A | C | A | C |
| 27 | 500 | A | A | A | A | A | B |
| 28 | 500 | B | A | A | A | A | C |
| 29 | 500 | A | A | A | A | A | C |
| 30 | 250 | C | A | A | C | — | C |
| 31 | 500 | C | C | A | C | C | C |
| 32 | 500 | B | A | A | A | A | C |
| 33 | 500 | C | A | B | A | A | C |

TABLE V

| CODE LETTERS (Table IV) | TEST SPECIES | SUPPORT MEDIUM/FOOD | TYPE OF TEST | DURATION (days) |
|---|---|---|---|---|
| NL | *Nilaparvata Lugens* (brown plant hopper) | Rice plant | CT | 3 |
| MD | *Musca domestica* (houseflies - adults) | Cotton wool/ sugar | CT | 1 |
| BG | *Blattella germanica* (cockroach nymphs) | Plastic pot calf weener pellets | RT | 3 |
| HV | *Heliothis virescens* | Cotton leaf | RT | 3 |
| CPA | *Chilo partellus* (maize stem bore) | Oil seed rape leaf | RT | 3 |
| DB | *Diabrotica balteata* (rootworm larvae) | Filter paper/ maize seed | RT | 3 |

CPH/jc
PP 33628
15 Aug 86

We claim:

1. A compound of formula:

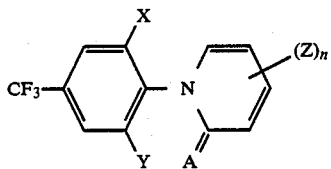

(I)

wherein each of X and Y independently represents halo, n is an integer from 1 to 4; each Z is independently selected from halo and trihalomethyl, and A is oxygen or sulphur.

2. A compound according to claim 1 wherein n is 1 or 2.

3. A compound according to claim 1 wherein each X and Y independently represents chloro or fluoro.

4. A compound according to claim 2 wherein n is one and Z represents trifluoromethyl or n is two and at least one Z represents trifluoromethyl.

5. A compound according to claim 4 wherein A is oxygen.

6. A compound selected from 1-(2,6-difluoro-4-trifluoromethylphenyl)-4-trifluoromethyl-2-pyridone;
1-(2-Chloro-6-fluoro-4-trifluoromethylphenyl)-3-chloro-5-trifluoromethyl-2-pyridone;
1-(2-Chloro-6-fluoro-4-trifluoromethylphenyl)-3,5-dibromo-2-pyridone;
1-(2,6-Difluoro-4-trifluoromethylphenyl)-3-chloro-5-trifluoromethyl-2-pyridone;
1-(2,6-Difluoro-4-trifluoromethylphenyl)-5-chloro-2-pyridone;
1-(2,6-Difluoro-4-trifluoromethylphenyl)-3,5-bis(trifluoromethyl)-2-pyridone;
1-(2,6-Difluoro-4-fluoromethylphenyl)-5-chloro-4-trifluoromethyl-2-pyridone;
1-(2,6-Difluoro-4-trifluoromethylphenyl)-5-bromo-4-trifluoromethyl-2-pyridone;
1-(2-Chloro-6-fluoro-4-trifluoromethylphenyl)-4-trifluoromethyl-2-pyridone;
1-(2-Chloro-6-fluoro-4-trifluoromethylphenyl)-5-trifluoromethyl-2-pyridone;
1-(2-Chloro-6-fluoro-4-trifluoromethylphenyl)-5-chloro-2-pyridone;
1-(2-Chloro-6-fluoro-4-trifluoromethylphenyl)-3-bromo-2-pyridone;
1-(2-Chloro-6-fluoro-4-trifluoromethylphenyl)-3,5-dichloro-2-pyridone;
1-(2-Chloro-6-fluoro-4-trifluoromethylphenyl)-3,5-bis-(trifluoromethyl)-2-pyridone;
1-(2-Chloro-6-fluoro-4-trifluoromethylphenyl)-5-bromo--trifluoromethyl-2-pyridone;
1-(2-Chloro-6-fluoro-4-trifluoromethylphenyl)-4,5-bis(-trifluoromethyl)-2-pyridone;
1-(2-Chloro-6-fluoro-4-trifluoromethylphenyl)-3,5-dichloro-4-trifluoromethyl-2-pyridone;
1-(2-Chloro-6-fluoro-4-trifluoromethylphenyl)-3,5-dibromo-4-trifluoromethyl-2-pyridone;
1-(2,6-Dichloro-4-trifluoromethylphenyl)-3-chloro-5-trifluoromethyl-2-pyridone;
1-(2,6-Dichloro-4-trifluoromethylphenyl)-3,5-bis(trifluoromethyl)-2-pyridone;
1-(2,6-Dichloro-4-trifluoromethylphenyl)-4-trifluoromethyl-2-pyridone;
1-(2,6-Dichloro-4-trifluoromethylphenyl)-4-chlorodifluoromethyl-2-pyridone;
1-(2,6-Dichloro-4-trifluoromethylphenyl)-5-chloro-4-trifluoromethyl-2-pyridone;
1-(2,6-Dichloro-4-trifluoromethylphenyl)-5-bromo-4-trifluoromethyl-2-pyridone;

1-(2,6-Dichloro-4-trifluoromethylphenyl)-4,5-bis-(trifluoromethyl)-2-pyridone;

1-(2,6-Dichloro-4-trifluoromethylphenyl)-3,5-dichloro--trifluoromethyl-2-pyridone;

1-(2-Bromo-6-chloro-4-trifluoromethylphenyl)-4-trifluoromethyl-2-pyridone;

1-(2,6-Dibromo-4-trifluoromethylphenyl)-4-trifluoromethyl-2-pyridone;

1-(2,6-Difluoro-4-trifluoromethylphenyl)-5-trifluoromethyl-2-pyridone;

1-(2,6-Difluoro-4-trifluoromethylphenyl)-3,5-dichloro--pyridone;

1-(2,6-Difluoro-4-trifluoromethylphenyl)-3-bromo-5-trifluoromethyl-2-pyridone;

1-(2-Chloro-6-fluoro-4-trifluoromethylphenyl)-5-chloro-4-trifluoromethyl-2-pyridone;

1-(2,6-Dichloro-4-trifluoromethylphenyl)-4-trifluoromethyl-2-pyridone.

7. A compound of formula (IIIA) or (IIIB)

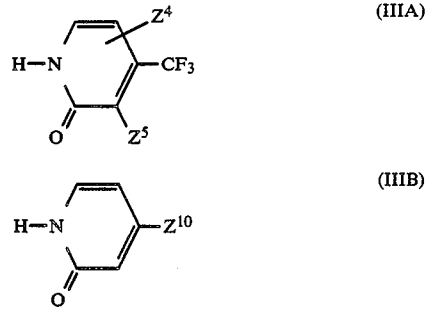

where $Z^4$ and $Z^5$ are independently selected from hydrogen, halogen, or trifluoromethyl provided that $Z^4$ and $Z^5$ are not both hydrogen; and $Z^{10}$ is trihalomethyl other than trifluoromethyl.

8. An insecticidal composition comprising as active ingredient an insecticidally effective amount of a compound according to claim 1.

9. A method of combating insect pests which comprises applying to the pest or to a locus thereof an insecticidally effective amount of a composition according to claim 8.

* * * * *